(12) United States Patent
Lepilleur

(10) Patent No.: US 7,704,934 B2
(45) Date of Patent: Apr. 27, 2010

(54) CATIONIC CASSIA DERIVATIVES AND APPLICATIONS THEREFOR

(75) Inventor: Carole A. Lepilleur, Akron, OH (US)

(73) Assignee: Lubrizol Advanced Marterials, Inc., Cleveland, OH (US)

(*) Notice: Subject to any disclaimer, the term of this patent is extended or adjusted under 35 U.S.C. 154(b) by 0 days.

(21) Appl. No.: 12/254,437

(22) Filed: Oct. 20, 2008

(65) Prior Publication Data

US 2009/0047227 A1 Feb. 19, 2009

Related U.S. Application Data

(63) Continuation of application No. 11/843,920, filed on Aug. 23, 2007, now Pat. No. 7,439,214, which is a continuation of application No. 10/874,296, filed on Jun. 18, 2004, now Pat. No. 7,262,157.

(60) Provisional application No. 60/479,793, filed on Jun. 19, 2003.

(51) Int. Cl.
*C11D 3/22* (2006.01)
*C11D 3/37* (2006.01)
*C11D 1/38* (2006.01)
*A61K 8/73* (2006.01)

(52) U.S. Cl. .......... 510/121; 510/123; 510/151; 510/470; 510/504; 424/488; 424/70.13; 424/78.03

(58) Field of Classification Search .......... 510/121, 510/123, 151, 470, 504; 424/488, 70.13, 424/78.03

See application file for complete search history.

(56) References Cited

U.S. PATENT DOCUMENTS

| 4,661,475 A | 4/1987 | Bayerlein et al. |
| 4,753,659 A * | 6/1988 | Bayerlein et al. ............ 8/561 |
| 5,733,854 A * | 3/1998 | Chowdhary et al. ........ 510/121 |

FOREIGN PATENT DOCUMENTS

| DE | 10047278 | 4/2002 |
| WO | WO 03/008456 | 1/2003 |

* cited by examiner

*Primary Examiner*—Brian P Mruk
(74) *Attorney, Agent, or Firm*—Thoburn T. Dunlap

(57) ABSTRACT

This invention relates to cationically derivatized polycalactomannans obtained from *cassia tora* and *cassia obtusifolia* and to their use in personal care, household care, and institutional care compositions.

22 Claims, No Drawings

CATIONIC CASSIA DERIVATIVES AND APPLICATIONS THEREFOR

CROSS REFERENCE TO RELATED APPLICATION

This application is a continuation application of U.S. application Ser. No. 11/843,920 filed on Aug. 23, 2007, now U.S. Pat. No. 7,439,214 which is a continuation of U.S. Ser. No. 10/874,296 filed on Jun. 18, 2004 now U.S. Pat. No. 7,262,157 which issued Aug. 28, 2007, and claims priority from U.S. Provisional Application Ser. No. 60/479,793 filed on Jun. 19, 2003.

TECHNICAL FIELD

This invention generally relates to polygalactomannan derivatives. More specifically, the invention relates to cationically derivatized galactomannan polymers obtained from *Cassia tora* and *Cassia obtusifolia* and their use in personal care, health care, household, institutional and industrial products and the like. The cationically derivatized galactomannan polymers can be employed as thickeners, stabilizers, emulsifiers, spreading aids and carriers for enhancing the efficacy, deposition and delivery of chemically and physiologically active ingredients. In addition, these polymers are useful for improving the psychosensory and aesthetic properties of cosmetic formulations in which they are included.

BACKGROUND

Polygalactomannans are polysaccharides that are found in the endosperm material of seeds from leguminous plants such as *Cyamopsis tetragonoloba* (guar gum), *Cesalpinia spinosa* (tara gum), *Ceratonia siliqua* (locust bean gum), and other members of the Leguminosae family. A polygalactomannan is composed of backbone of 1→4-linked β-D-mannopyranosyl units with recurring 1→6-linked α-D-galactosyl side groups branching from the number 6 carbon of a mannopyranose residue in the backbone. The galactomannan polymers of the different Leguminosae species defer from one another in the frequency of the occurrence of the galactosyl side units branching from the polymannopyranose backbone. The average ratio of D-mannosyl to D-galactosyl units in the polygalactomannan contained in guar gum is approximately 2:1, approximately 3:1 for tara gum, and approximately 4:1 for locust bean gum. Another important source of polygalactomannan is *Cassia tora* and *Cassia obtusifolia* (collectively known as *cassia* gum). The average ratio of D-mannosyl to D-galactosyl units in the polygalactomannan contained in *cassia* gum is approximately 5:1.

Polygalactomannan obtained from *cassia* gum is schematically represented in the structure below:

wherein n represents an integer from about 15 to about 35. In another embodiment, n represents and integer from about 20 about 30. In still another embodiment of the invention, the polygalactomannan of in invention has a number average molecular weight ranging from about 200,000 to about 300,000 (GPC method using a polystyrene standard)

Polygalactomannans are hydrocolloids that have a high affinity for water. They have been widely used as suspending, thickening, emulsifying, and gelling agents in applications as diverse as foodstuffs, coatings, personal care compositions and in oil well fracturing fluids. Although the use of these polymers has been met with great success, polygalactomannans used in their natural form have suffered some drawbacks from a water solubility standpoint. An unsubstituted polymannose backbone is completely insoluble in water. The attachment of galactose side units to the C-6 atom in the recurring mannose residues of the polymannose backbone increases the water solubility of the polymer, particularly in cold water (i.e., ambient temperature and below). The greater the galactose side unit substitution, the greater is the cold water solubility properties of the polygalactomannan. Consequently, lower ratios of D-mannosyl to D-galactosyl units in the polygalactomannan leads to better cold water solubility. For example the polygalactomannan contained in guar gum (average D-mannosyl to D-galactosyl ratio 2:1) is soluble in cold water, while the polygalactomannan obtained from *cassia* gum (average D-mannosyl to D-galactosyl ratio of 5:1) is only sparingly soluble in cold and hot water.

U.S. Pat. No. 4,753,659 to Bayerlein et al. discloses inter alia that improved cold water solubility can be imparted to *cassia* gum by chemically modifying the polygalactomannan. The reaction of *cassia* gum polygalactomannan with selected reagents to yield C-6 substituted derivatives is disclosed. Exemplary reaction products include C-6 substituted and unsubstituted alkyl ethers, C-6 substituted phosphate esters, and C-6 substituted quaternary ammonium compounds. Disclosed uses for the chemically modified *cassia* gum polygalactomannans include textile printing applications, oil well drilling auxiliaries, mining and explosive applications.

U.S. Pat. No. 5,733,854 to Chowdhary et al. discloses a chemically modified guar gum and a method for its preparation. According to Chowdhary et al., cationically derivatized guar gum polygalactomannans produce clear and colorless solutions upon dispersal in aqueous or organic solvents. A disclosed application for the cationically derivatized guar gum includes its incorporation into detergent compositions for human and household uses. Other disclosed uses include personal care and cosmetic applications. The use of cationi-

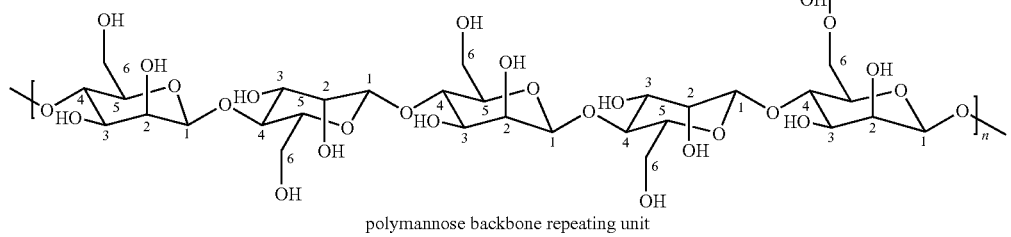

polymannose backbone repeating unit cally derivatized *cassia* gum in personal care, pharmaceutical, home care or cosmetic formulations is not discussed.

An inherent drawback with cationically derivatized guar gum polygalactomannans is the high ratio of galactose side units contained on the polymannose backbone. For every two mannose backbone repeating units there is one pendant galactose side unit. The galactose side units shield the hydroxyl groups contained on the C-6 atom of the mannose backbone units from access to derivation reagents. For the most part, only the C-6 hydroxyl group on the galactose side unit is accessible for functionalization by derivatizing agents. Consequently, the degree of cationic group substitution on the guar gum polygalactomannan is relatively low.

Accordingly, there exists is a need for a derivatized polygalactomannan with a high degree of molecular substitution which is suitable for use in thickener, stabilizer, emulsifier, spreading aid and carrier applications for enhancing the efficacy, deposition and delivery of chemically, cosmetically and physiologically active ingredients.

DESCRIPTION OF EXEMPLARY EMBODIMENTS

Exemplary embodiments in accordance with the present invention will be described. Various modifications, adaptations or variations of such exemplary embodiments described herein may become apparent to those skilled in the art as such are disclosed. It will be understood that all such modifications, adaptations or variations that rely upon the teachings of the present invention, and through which these teachings have advanced the art, are considered to be within the scope and spirit of the present invention.

In one aspect, embodiments of the present invention relate to polygalactomannan compositions that have been derivatized to higher degrees of molecular substitution than prior art polygalactomannan compositions. In some embodiments of the present invention a polygalactomannan isolated from the endosperm of the seeds of *Cassia tora* and *Cassia obtusifolia* (*cassia* gum) is post-functionalized to contain recurring pendant nonionic, anionic and cationic moieties. Some exemplary embodiments in accordance with the present invention relate to cationically modified *cassia* gum polygalactomannan. Other embodiments relate to molecularly substituted *cassia* gum polygalactomannans that are tailored for use as thickeners, stabilizers, emulsifiers, spreading aids and carriers for enhancing the efficacy, deposition and delivery of chemically and physiologically active ingredients. Yet other such embodiments relate to personal care, home care, food and industrial compositions that contain molecularly substituted *cassia* gum polygalactomannans.

As used here and throughout the specification, the terms molecularly substituted and molecular substitution mean appending a substituent selected from nonionic, anionic, cationic, and amphoteric containing moieties, as well as combinations thereof, to the C-6 carbon atom of the galactose side unit and/or to the C-6 carbon atom of the mannose repeating backbone units of the *cassia* gum derived polygalactomannan. Functionalization reagents containing these moieties are co-reacted with the hydroxyl group that is bonded to the C-6 carbon atom of the galactose and mannose residues that make up the *cassia* gum derived polygalactomannan. In other words, a hydroxyl hydrogen is replaced by a moiety derived from the functionalization reagent. In one embodiment, the hydroxyl hydrogen on the C-6 carbon atom is replaced by a moiety derived from the functionalization reagent. The reaction is schematically represented below:

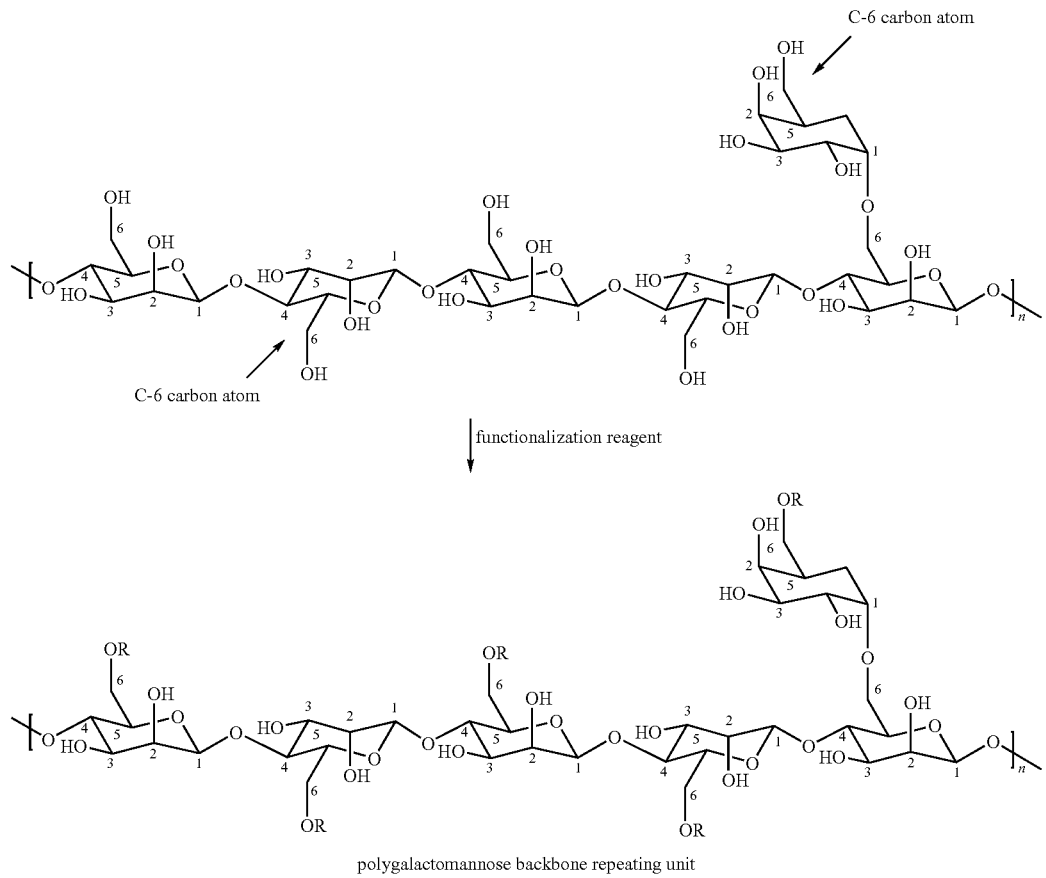

polygalactomannose backbone repeating unit

In some embodiments of the invention, R independently represents hydrogen, a nonionic group, an anionic group, a cationic group, and an amphoteric group, subject to the proviso that all R groups can not be hydrogen at the same time. In other embodiments, R independently is selected from the formula:

-AR$^1$ wherein A is an alkylene spacer group containing 1 to 6 carbon atoms and R$^1$ represents a nonionic substituent, an anionic substituent, a cationic substituent, and an amphoteric substituent. In another embodiment the alkylene group contains 2, 3, 4, or 5 carbon atoms. The alkylene spacer is optionally mono-substituted or multi-substituted with a group selected from C$_1$ to C$_3$ alkyl, C$_1$ to C$_3$ haloalkyl, C$_1$ to C$_3$ hydroxyalkyl, hydroxyl, halogen (bromine, chlorine, fluorine, and iodine), and combinations thereof. An exemplary nonionic R$^1$ substituent is —OH. Illustrative nonionic groups defined under -AR$^1$ can be represented by the formula:

-alkylene-OH wherein the alkylene spacer is defined above. Representative nonionic groups include but are not limited to hydroxymethyl, hydroxyethyl, hydroxypropyl, and hydroxybutyl.

Exemplary anionic R$^1$ substituents are —COOH, —SO$_3$H, —OP(O)(OH)(OH), and —P(O)(OH)(OH). Illustrative anionic groups defined under -AR$^1$ can be represented by the formulae:

-alkylene-COOH

-alkylene-SO$_3$H

-alkylene-OP(O)(OH)(OH)

-alkylene-P(O)(OH)(OH)

wherein the alkylene spacer is as defined previously. Representative anionic groups include but are not limited to carboxymethyl, carboxyethyl, and carboxypropyl.

Exemplary cationic substituents under R$^1$ includes 1°, 2°, and 3° amines represented by the radical: —N(R$^2$)$_2$, and quaternary ammonium, sulfonium and phosphonium derivatives represented by the radicals: —N(R$^3$)$_3{}^+$X$^-$, —S(R$^3$)$_2{}^+$X$^-$, —P(R$^3$)$_3{}^+$X$^-$, wherein R$^2$ independently represents hydrogen, linear and branched C$_1$ to C$_5$ alkyl, phenyl and benzyl; R$^3$ independently represents C$_1$ to C$_{24}$ alkyl, benzyl and phenyl; and X is any suitable anion that balances the charge on the onium cation. In one embodiment, X is a halide anion selected from bromine, chlorine, fluorine and iodine. The alkyl, benzyl and phenyl substituents defined under R$^2$ and R$^3$ can optionally be mono-substituted or multi-substituted with a group selected from C$_1$ to C$_3$ alkyl, hydroxyl, halogen (bromine, chlorine, fluorine, and iodine), and combinations thereof. Illustrative cationic groups defined under -AR$^1$ can be represented by the formulae:

-alkylene-N(R$^2$)$_2$

-alkylene-N(R$^3$)$_3{}^+$X$^-$

-alkylene-S(R$^3$)$_2{}^+$X$^-$

-alkylene-P(R$^3$)$_3{}^+$X$^-$ wherein alkylene, R2, R3, and X are as previously defined. Representative of cationic groups under -AR$^1$ are quaternary ammonium groups that include but are not limited to the formula:

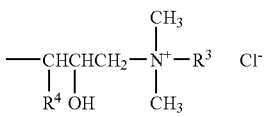

wherein R$^3$ is selected from methyl, decyl, dodecyl, butadecyl, cocoalkyl, dodecyl, and octadecyl, and R$^4$ is selected from hydrogen and chlorine.

The amphoteric substituents can be selected from any radical or residue that contains both a positive and negative charge. Representative amphoteric substituents include betaine, amino acid, dipeptides, tripeptide and polypeptide residues.

Underivatized *Cassia* gum or flour is commercially available from Noveon, Inc. under the Diagum trademark. As discussed supra, the derivatization of *cassia* gum polygalactomannan occurs at the C-6 hydroxyl group on the galactose side unit and/or on the backbone mannose repeating units. The steric hindrance of the galactose side unit controls the amount of substitution that can occur at the C-6 hydroxyl group in polygalactomannans. *Cassia* gum polygalactomannans differ from other polygalactomannans in the degree of substitution at the C-6 hydroxyl group since the structure of *cassia* affords more accessibility (i.e., less steric hindrance) of the C-6 hydroxyl reactive site, resulting in higher degrees of functional group substitution. In embodiments of the invention wherein ionic group substitution is effected the derivatized *cassia* gum polygalactomannan will have a broader range of charge density when compared to the similarly derivatized prior art polygalactomannans. In some embodiments of the invention the degree of quaternary ammonium cationic substitution can range up to 60% and above. The term "degree of substitution" refers to the percentage of available C-6 hydroxyl groups per polygalactomannan repeating unit (represented by the bracketed repeating unit structure above) that have been modified with the modifying substituent (e.g., 3 out of the 5 available C-6 hydroxyl groups are modified). In comparison, the derivatized prior art guar polygalactomannans exhibit a degree of substitution of only 33%.

The derivatization of the *Cassia* polygalactomannan C-6 hydroxyl group can be accomplished by methods well known to those skilled in the art. Generally speaking, the C-6 hydroxyl group can be reacted with any functionalization reagent that is co-reactive therewith. For example, to functionalize the C-6 hydroxyl group with the nonionic, anionic, cationic and amphoteric substituents of the invention, the C-6 hydroxyl group(s) on the *Cassia* gum polygalactomannan are reacted with a functionalization reagent that contains the respective nonionic, anionic, cationic and amphoteric substituents and a functional moiety that is co-reactive with the C-6 hydroxyl group. The functionalization reaction is conducted in an appropriate solvent and at an appropriate temperature. The amount of functional group substitution (degree of substitution) on the polygalactomannan C-6 hydroxyl atom(s) can be controlled by adjusting the stoichiometric amount of functionalization reagent added to the *Cassia* polygalactomannan. Functionalization methods for *Cassia* gum polygalactomannans are disclosed in U.S. Pat. No. 4,753,659 which is incorporated herein by reference. Additional methods of derivatizing polygalactomannans are set forth in U.S. Pat. No. 5,733,854.

In an exemplary reaction *Cassia* gum polygalactomannan can be functionalized with co-reactive quaternary ammonium compounds which contain an epoxy group or a halohydrin group. In one such embodiment *Cassia* polygalactomannan can reacted with glycidyltrimethylammonium chloride (75% aqueous solution) in an alkaline aqueous medium at a temperature of about 52° C. to yield the desired 2-hydroxy-3-(trimethylammonium)propyl *Cassia* galactomannan chloride product. The reaction is schematically represented below:

aids and carriers for enhancing the efficacy, deposition and delivery of chemically and physiologically active ingredients and cosmetic materials, and as a vehicle for improving the psychosensory and aesthetic properties of a formulation in which they are included. The term "personal care products" as used herein includes, without limitation, cosmetics, toiletries, cosmeceuticals, beauty aids, personal hygiene and cleansing

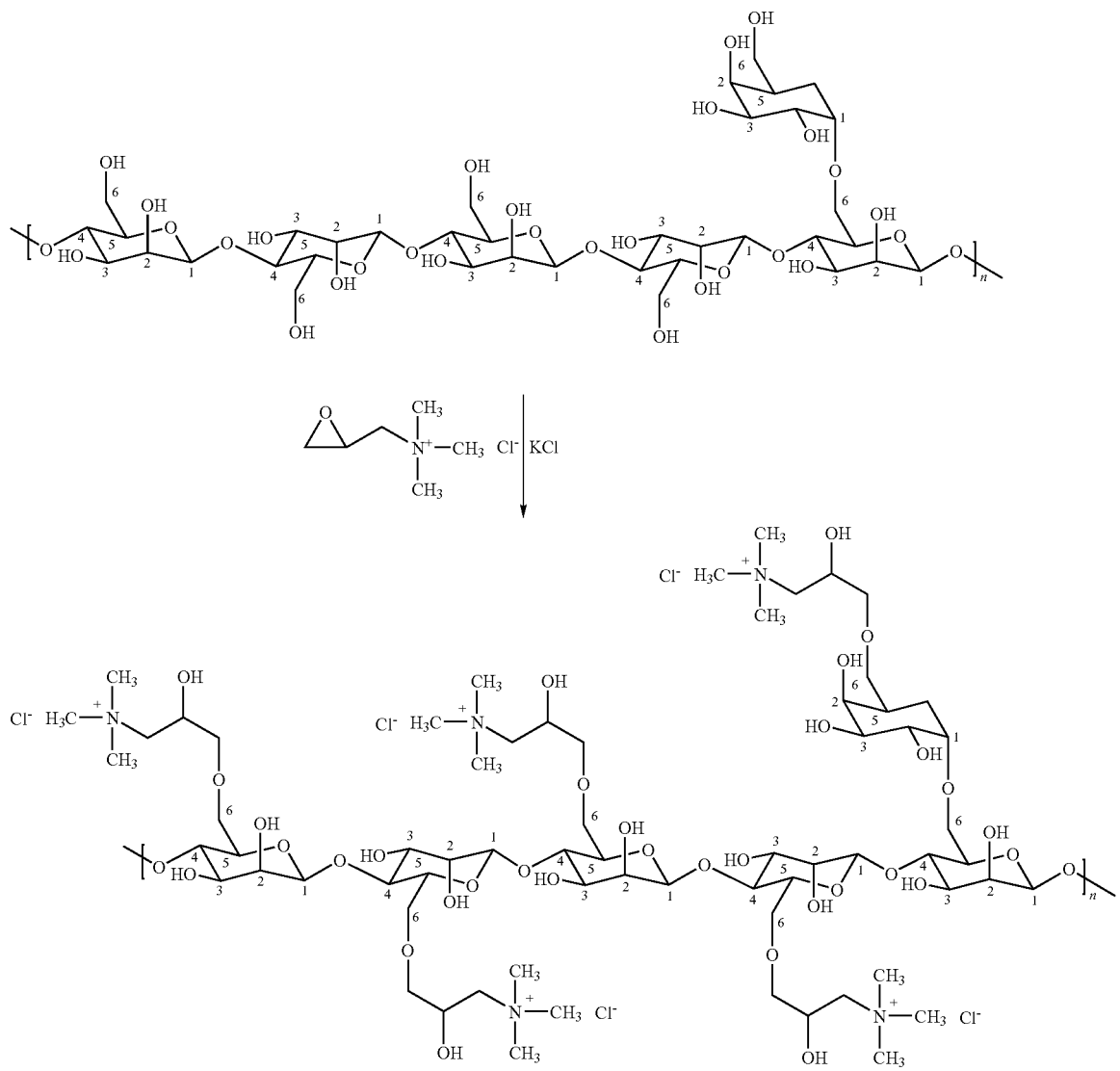

Chemical modification of *Cassia* gum leads to incorporation of nonionic, anionic, cationic, and amphoteric moieties, and combinations thereof onto the backbone. The chemical modification leads to various physical properties changes. For instance, derivatized *cassia* gums exhibit cold water or improved cold water solubility. It is able to hydrate in cold water and build viscosity by forming a colloidal thixotopic dispersion in cold water.

Some embodiments of the invention relate to the use of cationic *cassia* derivatives as multi-functional polymer ingredients in personal care, health care, household, institutional and industrial product applications and the like. The cationic *cassia* polymers can be employed as emulsifiers, spreading products that are applied to the skin, hair, scalp, and nails of humans and animals. The term "health care products" as used herein includes, without limitation, pharmaceuticals, pharmacosmetics, oral care products (mouth, teeth), eye care products, ear care products and over-the-counter products and appliances, such as patches, plasters, dressings and the like. The term also includes medical devices that are externally applied to or into the body of humans and animals for ameliorating a health related or medical condition. The term "body" includes the keratinous (hair, nails) and non-keratinous skin areas of the entire body (face, trunk, limbs, hands and feet), the tissues of body openings and the eyes. The term "skin" includes the scalp and mucous membranes. The term "household care products" as used herein includes, without limitation, products being employed in a household for surface protection and/or cleaning including biocidal cleaning products for maintaining sanitary conditions in the kitchen and bathroom and laundry products for fabric cleaning and the like. The term "institutional and industrial products" as used herein includes, without limitation, products employed for protection and/or cleaning or maintaining sanitary conditions in industrial and institutional environments, including hospitals and health care facilities, and the like.

In a given composition or application, the cationic *cassia* derivatives of this invention can, but need not, serve more than one function, such as a thickener and conditioner, film former and carrier or deposition aid, and the like. The amount of cationic *cassia* derivatives that can be employed depends upon the purpose for which they are included in the formulation and can be determined by person skilled in the formulation arts. Thus, as long as the physicochemical and functional properties are achieved, a useful amount of cationic *cassia* derivatives on a total composition weight basis, typically can vary in the range of about 0.01% to about 25%, but is not limited thereto.

Compositions containing cationic *cassia* derivatives can be packaged and dispensed from containers such as jars, tubes, sprays, wipes, roll-ons, sticks and the like, without limitation. There is no limitation as to the form of the product in which these derivatives can be incorporated, so long as the purpose for which the product is used is achieved. For example, personal and health care products containing cationic *cassia* derivatives can be applied to the skin, hair, scalp, and nails, or to hard surfaces or laundry fabrics, without limitation in the form of gels, sprays (liquid or foams), emulsions (creams, lotions, pastes), liquids (rinses, shampoos), bars, ointments, suppositories, and the like.

The cationic *cassia* derivatives of this invention are suitable for preparation of personal care (cosmetics, toiletries, cosmeceuticals) and topical health are products, including, without limitation, hair care products (shampoos, combination shampoos, such as "two-in-one" conditioning shampoos), post-shampoo rinses, setting and style maintenance agents (including setting aids, such as gels and sprays, grooming aids such as pomades, conditioners, perms, relaxers, hair smoothing products, and the like), skin care products (facial, body, hands, scalp and feet), such as creams, lotions and cleansing products, antiacne products, antiaging products (exfoliant, keratolytic, anticellulite, antiwrinkle, and the like), skin protectants (sun care products, such as sunscreens, sunblock, barrier creams, oils, silicones and the like), skin color products (whiteners, lighteners, sunless tanning accelerators and the like), hair colorants (hair dyes, hair color rinses, highlighters, bleaches and the like), pigmented skin colorants (face and body make-ups, foundation creams, mascara, rouge, lip products, and the like) bath and shower products (body cleansers, body wash, shower gel, liquid soap, soap bars, syndet bars, conditioning liquid bath oil, bubble bath, bath powders, and the like), nail care products (polishes, polish removers, strengtheners, lengtheners, hardeners, cuticle removers, softness, and the like).

Toiletries and health and beauty aids containing cationic *cassia* derivatives, can include, without limitation, hair-removal products (shaving creams and lotions, epilators, after-shaving skin conditioner, and the like); deodorants and antiperspirants; oral care products (mouth, teeth, gums), such as mouth wash, dentifrice, such as toothpaste, tooth powder, tooth polishes, tooth whiteners, breath fresheners, denture adhesives, and the like; facial and body hair bleach and the like. Other health and beauty aids can contain cationic *cassia* derivatives, include, without limitation, sunless tanning applications containing artificial tanning accelerators, such as dihydroxyacetone (DHA), tyrosine, tyrosine esters and the like: skin depigmenting, whitening and lightening, formulations containing such active ingredients as kojic acid, hydroquinone, arbutin, fruital, vegetable or plant extracts, (lemon peel extract, chamomile, green tea, paper mulberry extract, and the like), ascorbyl acid derivatives ascorbyl palmitate, ascorbyl stearate, magnesium ascorbyl phosphate and the like); foot care products, such as keratolytic corn and callous removers, foot soaks, foot powders (medicated such as antifungal athlete's foot powder, ointments, sprays, and the like, antiperspirant powders, or non-medicated moisture absorbent powder), liquid foot sprays (non-medicated, such as cooling, and deodorants sprays, and the like), and foot and toenail conditioners (lotions, creams, nails softeners, and the like).

Topical health and beauty aids can include cationic *cassia* derivatives as spreading aids and film formers include, without being limited thereto, skin protective sprays, cream, lotion, gels, stick, powder products such as insect repellants, itch relief, antiseptics, disinfectants, sun blocks, sun screens, skin tightening and toning milk and lotions, wart removal compositions, and the like.

Cationic *cassia* derivatives are particularly useful as suspending agents for particulates making them suitable for dermal products containing particulates, microabrasives, and abrasives, such as shower gels, masks and skin cleansers containing exfoliative scrub agents. Typical particulates include, but are not limited thereto, shell, seed, and stone granules, such as almonds, apricot (seed, kernel powder, shell), avocado, coconut, corn cob, olive, peach, rose hip seed, walnut shell, and the like, aluminum silicate, jojoba (wax, seed powder), oyster shell powder, evening primrose seed, milled adzuki beans, and the like, polyethylene (granules, spheres), polyethylene (and) hydroxycellulose granules, microcrystalline cellulose, polystyrene, polystyrene (and) talc granules, ground pumice, ground loofah, ground seaweed, rice, oat bran, silica (hydrated, colloidal, and the like), ground eggshell, ground blue poppy seed, salt, such as sodium chloride, dead sea salt, and the like, and mixtures thereof.

Cationic *cassia* derivatives are useful as thickeners and film formers in a variety of dermatological, cosmeceutical compositions employed for topically ameliorating skin conditions caused by aging, drying, photodamage, acne, and the like, containing conditioners, moisturizers, antioxidants, exfoliants, keratolytic agents, vitamins, and the like. Cationic *cassia* derivatives can be employed as a thickener for active skin treatment lotions and creams, containing as such active ingredients, acidic anti-aging agents, anti-cellulite, and anti-acne agents, such as alpha-hydroxy acid (AHA), beta-hydroxy acid (BHA), alpha amino-acid, alpha-keto acids (AKAs), and mixtures thereof. In such cosmeceuticals, AHAs can include, but are not limited to, lactic acid, glycolic acid, fruit acids, such as malic acid, citric acid, tartaric acid, extracts of natural compounds containing AHA, such as apple extract, apricot extract, and the like, honey extract, 2-hydroxyoctanoic acid, glyceric acid (dihydroxypropionic acid), tartronic acid (hydroxypropanedioic acid), gluconic acid, mandelic acid, benzilic acid, azelaic acid, acetic acid, alpha-lopioc acid, salicylic acid, AHA salts and derivatives, such as arginine glycolate, ammonium lactate, sodium lactate, alpha-hydroxybutyric acid, alpha-hydroxyisobutyric acid, alpha-hydroxyisocaproic acid, alpha-hydroxyisovaleric acid, atrolactic acid, and the like. BHAs can include, but are not limited to, 3-hydroxy propanoic acid, beta-hydroxybutyric acid, beta-phenyl lactic acid, beta-phenylpyruvic acid, and the like. Alpha-amino acids include, without being limited to, alpha-amino dicarboxylic acids, such as aspartic acid, glutamic acid, and mixtures thereof, sometimes employed in combination with fruit acids. AKAs include pyruvic acid. In some antiaging compositions, the acidic active agent may be retinoic acid, a halocarboxylic acid, such as trichloroacetic acid, an acidic antioxidant, such as ascorbic acid (vitamin C), a mineral acid, phytic acid, lysophosphatidic acid, and the like. Some antiacne agents, for example, can include salicylic acid, derivatives of salicylic acid, such as 5-octanoylsalicylic acid, retinoic acid and its derivatives.

Other health care products in which cationic *cassia* derivatives can be included are medical products, such as topical and non-topical pharmaceuticals and devices. In the formulation of pharmaceuticals, a cationic *cassia* derivatives can be used as a thickener and/or lubricant in such products as creams, pomades, gels, pastes, ointments, tablets, gel capsules, purgative fluids (enemas, emetics, colonics, and the like), suppositories, anti-fungal foams, eye products (ophthalmic products such as eyedrops, artificial tears, glaucoma drug delivery drops, contact lens cleaner, and the like), ear products (wax softeners, wax removers, otitis drug delivery drops, and the like), nasal products (drops, ointments, sprays, and the like), wound care (liquid bandages, wound dressings, antibiotic creams, ointments and the like), without limitation thereto.

The cationic *cassia* derivatives can be used in home care, institutional and industrial applications (I&I), as a rheology modifier, fabric conditioning agent, especially to improve efficiency through "cling-on surface" or improving efficacy of disinfectants, and biocidal formulations, and to synergistically improve fabric softening efficacy in combination with traditional fabric softeners. Typical household and I&I products that may contain cationic *cassia* derivatives, include, without limitation, laundry and fabric care products, such as detergents, fabric softeners (liquid or sheet), ironing sprays, dry cleaning aids, anti-wrinkle sprays, spot removers and the like; hard surface cleaners for the kitchen and bathroom and utilities and appliances employed or located herein, such as toilet bowl gel, tub and shower cleaners, hard water deposit removers, floor and tile cleansers, wall cleansers, floor and chrome fixture polishes, alkali-strippable vinyl floor cleaners, marble and ceramic cleaners, air freshener gels, liquid cleansers for dishes, and the like; disinfectant cleaners, such as toilet bowl and bidet cleaners, disinfectant hand soap, room deodorizers, and the like.

The cationic *cassia* derivatives can be used as rheology modifiers, dispersants, stabilizers, promoters, and the like, in industrial product applications, such as, without limitation, textiles processing, finishing, printing, and dyeing aids, protective washable surface coatings, manufacture of synthetic leather by saturation of non-woven fabrics, and the like, of woven or non-woven fabrics and natural or synthetic fibers); water treatment (waste water, cooling water, potable water purification, and the like): chemical spills containment (acid-spill absorbent, and the like); leather and hides (processing aids, finishing, embossing and the like); paper and papermaking (surface coating, such as pigmented coatings, antistatic coatings and the like, pulp binders, surface sizing, dry and wet strength enhancers, manufacture of synthetic fibers, such as non-woven fabrics, wet-laid felts, and the like): printing (inks, antiwicking ink-jet printer inks, thickeners for ink formulations containing cationic dyes for printing acrylic fabrics, and the like); paints (pigments and grinding additives, crosslinking agents for epoxy latex emulsions, particulate-suspending aids for clays, pigments and the like); industrial plant effluent treatment (flocculants for phenolics in paper mill effluent, and the like); metal working (acid etch cleaners, low pH metal coatings, pickling agents in cold rolled steel processing, and the like); wood preservation: and industrial construction products for buildings and roads (cement plasticizers, asphalt emulsions stabilizers at low pH, acid etch for cement, consistency modifiers of concrete, mortar, putty and the like). The cationic *cassia* derivatives are also useful as thickeners for rust removers, acid truck cleaners, scale removers, and the like, and as dispersion stabilizers of products containing particulates, such as clay, pigments (titanium dioxide, calcium carbonate, and other minerals), abrasives, and the like, employed in a variety of foregoing industrial applications and in drilling muds and oil well fracturing fluids.

The foregoing products typically contain various conventional additives and adjuvants known in the art, some of which can serve more than one function. The amounts employed will vary with the purpose and character of the product and can be readily determined by one skilled in the formulation arts and from the literature.

It is known that formulated compositions for personal care and topical, dermatological, health care, which are applied to the skin and mucous membranes for cleansing or soothing, are compounded with many of the same or similar physiologically tolerable ingredients and formulated in the same or similar product forms, differing primarily in the purity grade of ingredients selected, by the presence of medicaments or pharmaceutically accepted compounds, and by the controlled conditions under which products may be manufactured. Likewise, many of the ingredients employed in the products for household and I&I are same or similar to the foregoing, differing primarily in the amounts and material grades employed. It is also known that the selection and permitted amount of ingredients also may subject to governmental regulations, on a national, regional, local, and international level. Thus, discussions herein of various useful ingredients for personal care and health care products may apply to household and I&I products and industrial applications.

The choice and amount of ingredients in formulated compositions containing cationic *cassia* derivatives polymer will vary depending on the product and its function, as is well known to those skilled in the art. Formulation ingredients for personal care and topical health care products can typically include, but are not limited to, solvents, surfactants (as cleansing agents, emulsifying agents, foam boosters, hydrotropes, solubilizing agents, and suspending agents), non-surfactant suspending agents, emulsifiers, skin conditioning agents (emollients, moisturizers, and the like), hair conditioning agents (including silicones and silicone oils), hair fixatives, film-formers, skin protectants, binders, chelating agents, antimicrobial agents, antifungal agents, antidandruff agents, abrasives, adhesives, absorbents, colorants, deodorants agents, antiperspirant agents, humectants, opacifying and pearlescing agents, antioxidants, preservatives, propellants, spreading agents, sunscreen agents, sunless skin tanning accelerators, ultraviolet light absorbers, pH adjusting agents, botanicals, hair colorants, oxidizing agents, reducing agents, skin bleaching agents, pigments, physiologically active agents, anti-inflammatory agents, topical anesthetics, fragrance and fragrance solubilizers, and the like, in addition to ingredients previously described that may not appear herein. Oral care products, for instance, can contain anti-caries, anti-tartar and/or anti-plaque agents in addition to surfactants, abrasives, humectants, fillers, and flavorants. An extensive listing of substances and their conventional functions and product categories appears in the CFTA Dictionary, generally, and in Vol 2, section 4 and 5, in particular.

Due its water swelling properties, cationic *cassia* derivatives are often used as a gelling agent for water-based systems. For instance, cationic *cassia* derivatives can be used as gelling agents for air treatment gels that are designed to release continuously volatile air treatment agents from the gel. The volatile air treatment components can include air freshening ingredients such as disinfectants, bactericides, insecticides, fungicides, deodorants, pest repellants, odoriferous materials and mixtures thereof. Odoriferous materials include oil of rose, oil of lime, oil of lemon, oil of spearmint, oil of wintergreen, oil of cedar wood, oil of fir Canadian and the like. These oils may be used in combination with fragrances such as aromatic esters, aldehydes, ketones, and other compounds known to those skilled in the art of blending fragrances. The level of the gelling agent ranges from about 0.5 to about 25 wt. % in one embodiment, from about 0.75 to about 15 wt. % in another embodiment, and from about 1 to 5 wt. % in a further embodiment, wherein the weight percents are based on the total weight of the composition.

Cationic *cassia* derivatives can also be used to form hydrocolloid gels for wound dressing and medical devices. The healing of wounds such as wounds resulting from injury, surgery etc. is greatly dependent upon the dressing used. Conventional bandages often do not provide optimum results. Special pressure relieving or reducing measures should also be taken. A moist dressing is also often beneficial, providing rehydration of dehydrated tissue, increased angiogenesis (proliferation of new blood vessels), minimal bacterial growth, physical protection, and the maintenance of the proper pH for stimulating the release of oxygen and for allowing proteolytic enzymes to work more efficiently.

Pourable water based natural or synthetic water-soluble or water swellable gel forming hydrocolloidal gels can be used for wound dressing. They are initially sufficiently fluid to be poured or spread onto the wound, but, which after application can form a moist solid elastic protective gel that remains in the polymeric hydrocolloid hydrated state.

Medical devices adapted for implanting into the body to facilitate the flow of bodily fluids, to serve as vascular grafts or for other purposes have been developed. Typically, these devices include stents, catheters, or cannulas, plugs, constrictors, tissue or biological encapsulants and the like. Many of these devices that are used as implants are made from durable, non-degradable plastic materials such as polyurethanes, polyacrylates, and silicone polymers, and the like. In some instances they are made from biodegradable polymers, which remain stable in-vivo for a period of time, but eventually biodegrade into small molecules that are easily excreted form the body. Cross-linked hydrogels made from the cationic modified *Cassia* gum polygalactomannans are contemplated for use for such medical devices. They offer excellent biocompatibility and have been shown to reduce tendency for inducing thrombosis, encrustation and inflammation. In these applications, the hydrocolloidal polymeric gel that is used for wound healing or implants is the cationic *cassia* derivative. The cationic *cassia*-containing compositions, mixed with water, will form a solid temperature irreversible elastic gel, i.e. flexible gel, with or without crosslinking agents, to assist in the formation of a non-fluid system. Typical gels contain from 3 to 15 wt % cationic *cassia* derivatives. A greater amount of polymer and crosslinking agents will provide a more solid gel, or a gel that will display better physical and mechanical properties (modulus, stress at yield, strength). Sufficient water should be present to provide the initial fluidity required for pouring or spreading the gel onto the wound, or inserting the gel in the body through an endoscope, in the case of implants. Ionic and non-ionic cross-linkers are used then to solidify the gel, and control the crosslinking density (i.e., the final mechanical and physical properties of the gel). For most applications, the crosslinking agents are present from 0 to 8 wt %, more preferably from 0.1 to 5 wt %. Any suitable non-toxic crosslinker can be used, including galactose, mannose, oligosaccharides containing either or both mannose and galactose, borax, organic titanate, boric acid, diepoxides, polycarboxylic acids, glutaraldehyde, dihydroxyaluminum, sodium carbonate, citric acid, and a soluble source of any of the cations of calcium, magnesium and aluminum. In the case of implants, the ionic crosslinks can be easily and selectively displaced in-vivo after implantation of the implant device in the body, resulting in a swelling and softening of the device in the body which enhances patient comfort. The device will retain its original configuration without disintegration. If desired, any of the following substances can be included in the composition: medication and disinfectants, wound healing enhancers such as vitamins, blood coagulants, antibiotics, source of oxygen etc.

Cationic polymers are often used as conditioners in skin and/or hair compositions. Quaternized polymers are used in shampoos and conditioners to facilitate combability. The positively charged nitrogen bonds with negatively charged hair fibers to form films. They also make the hair feel softer and smoother to the touch without creating too much build-up. Cationic *cassia* derivatives can be used as part of a cationic polymer conditioner package in a conditioning detergent formulation that not only imparts cleansing, wet detangling, dry detangling and manageability properties to the hair, but also is relatively non-irritating. This composition is thus suitable for use by young children and adults having sensitive skin and eyes.

In skin care formulations, cationic *cassia* derivatives can be used as polymeric skin feel and skin mildness aids in ultra-mild skin cleansing compositions or moisturizing compositions. Cationic *cassia* derivatives provide skin conditioning, skin mildness and moisturizing, while maintaining desirable lathering properties. Cationic *cassia* derivatives also display a desirable silky, soft smooth in-use feeling, by avoiding less skin irritation though excessive defatting or over drying the skin after multiple usage. The positively charged cationic *cassia* derivatives can bind with negatively charged sites on the skin to provide a soft skin feel after use. It improves the sensory feel on skin by reducing tackiness and greasiness and improving smoothness.

Cationic *cassia* derivatives of this invention can be employed as a rheology modifier or emulsion stabilizing agents in emulsions. The cationic *cassia* derivatives of this invention provide better emulsion stability to foaming emulsion compositions. The need for a skin cleansing composition having good dermatological compatibility is growing. In particular, the use of an alkyl oligoglycoside as a non-ionic surfactant has found favor due to its favorable foaming and cleaning properties, biodegradability and dermatological compatibility. However, such alkyl oligoglycosides-containing emulsions lack cosmetic appeal. These compositions are not readily absorbed by the skin and instead of forming a creamy microfoam upon application to the skin, they only form a coarse macrofoam. Formulations containing cationic polymers such as cationic *cassia* derivatives lead to the formation of a rich and creamy microfoam that is readily absorbed by the skin with high cleaning and refatting properties.

Cleansing compositions that show good conditioning and lathering properties are highly desirable. This is difficult to achieve due to the inherent incompatibility between anionic surfactants (that show superior cleansing with high lathering compared to other surfactants) and the cationic polymers (that provides conditioning properties and/or aids in the deposition of therapeutic agents to the skin or hair). The presence of such anionic surfactants in the cleansing composition also interferes with the deposition of therapeutic agents because such compositions are designed to remove oil, grease and dirt and particulate matter from the hair, scalp and skin during rinsing. In personal care applications, the cationic *cassia* derivatives of the invention can be used along with surfactant, water-soluble agents (for instance silicones) to provide an enhanced delivery system for therapeutic agents, conditioners, moisturizers etc. Examples of therapeutic agents include, but are not limited to, detangling/wet combing agent, humectants, anti-acne agents, anti hair loss agents, hair-growth inhibitor agents, herbal extracts etc.

Various water-insoluble particulates (solid or liquid particles of oil emulsions) have been incorporated in detergent compositions for the purpose of imparting desirable residual properties on surfaces washed with such products. For instance, shampoo compositions containing particulate anti-dandruff agents can not function unless such agents are deposited and retained on the hair and scalp subsequent to rinsing. Particulate antimicrobial agents have also been used in various laundry detergents and personal care body washes to impart residual antimicrobial activity to fabrics and hair and skin surfaces. Various other water-insoluble or sparingly soluble particulate materials such as sunscreen agents, fabric softeners, fabric brighteners, fabric whiteners, etc., have also been employed in detergent compositions. Their activity depends on particle deposition and retention on washed substrates (skin, hair, fabrics, etc.). By its very nature an effective detergent composition tends to minimize retention of particulate matter on washed surfaces. Consequently, only a relatively small portion of the active agents present in detergent compositions is actually retained after washing and rinsing of the substrate surface. Since the activity of the active agent depends on the quantity of the particles deposited and retained on the surface, a means to enhance active agent deposition and retention are highly desirable. The cationic *cassia* derivatives of the present invention are suitable for such purposes.

In styling shampoo, the use of the cationic *cassia* derivatives of the present invention as deposition aids to enhance the deposition of water-insoluble styling polymers improves the styling performance (conditioning, curl retention, superior hair feel) of the hair. The cationic *cassia* derivatives of the invention can be used as deposition aids in combination with water-insoluble hair styling polymers selected from the group of (meth)acrylates copolymers and silicone-grafted (meth) acrylates. Examples include t-butylacrylate/2-ethylhexylacrylate copolymers, t-butylacrylate/2-ethylhexylmethacrylate copolymers, t-butyl acrylate/2-ethylhexyl methacrylate/polydimethylsiloxane macromer, and t-butyl methacrylate/2-ethylhexylmethacrylate/polydimethylsiloxane macromer copolymers, and mixtures thereof.

As previously discussed, various water-insoluble or sparingly soluble particulate materials such as sunscreens, fabric softeners, fabric brighteners, fabric whiteners, biocides, etc. are employed in cleaning compositions. Their activity will depend on the particle deposition and retention on washed systems. By its very nature, an effective detergent composition tends to minimize retention of particulate matters on washed surfaces. Thus, only a relatively small portion of the agents present in such detergent composition is actually retained after washing and rinsing of the surface. Since the activity of the functional agent depends on the quantity of the particles deposited and retained on the surface, means to enhance deposition are highly desirable. Cationic *cassia* derivatives can be used as a deposition aid for those particulate materials: for instance for depositing fabric softener on fabric surfaces during laundering process, or depositing biocides on hard surfaces during sanitization. For example, the use of cationic *cassia* derivatives along with regular laundry detergents ingredients such as surfactants, builders, etc., shows improvement in softening properties due to better deposition of the fabric softener on the surface and significantly more storage stability. From about 0.05 to about 5 wt. % of the overall composition is used for the cationic *cassia* derivatives as deposition aid. In one aspect of the invention when employed in a composition that includes a surfactant, the ratio of cationic *cassia* to surfactant can range from about 10:1 to about 1:10 (wt. to wt. basis).

Cationic *cassia* derivatives can also be used as a soil release agent in laundry detergent composition. During the laundering operation, these polymers absorb onto the surface of the fabric immersed in the wash solution. The absorbed polymer forms a hydrophilic layer which remains on the fabric after it is removed from the wash solution and dried, thereby imparting soil release properties to the laundering fabric. Low levels of cationic *cassia* derivatives (0.3 to 5 wt. %) in combination with typical fabric softeners can provide the soil release properties without adversely affecting the whiteness of fabric upon repeated usage.

What is claimed is:

1. A method for enhancing the deposition of a chemically, cosmetically, or physiologically active ingredient contained in a personal care or healthcare composition on a surface said method comprising including therein a cationically functionalized *cassia* galactomannan wherein a portion of the hydrogen groups in the pendant hydroxy groups of the *cassia* galactomannan are substituted with a group represented by the formula:

$$-AR^1$$

wherein A is a substituted or unsubstituted alkylene group containing 1 to 6 carbon atoms, and $R^1$ is a group independently selected from $-N(R^3)_3{}^+X^-$, $-S(R^3)_2{}^+X^-$, and $-P(R^3)_3{}^+X^-$, wherein $R^3$ independently represents substituted and unsubstituted $C_1$ to $C_{24}$ alkyl, substituted and unsubstituted benzyl and substituted and unsubstituted phenyl; and X is any suitable anion that balances the charge on the onium cation.

2. A method of claim 1 wherein said alkyl, alkylene, phenyl and benzyl groups are substituted mono-substituted or independently multi-substituted with a group selected from $C_1$ to $C_3$ alkyl, hydroxyl, and halogen.

3. A method of claim 1 wherein X is a halide.

4. A method of claim 1 wherein at least one C-6 hydroxyl hydrogen is substituted by the $-AR^1$ substituent.

5. A method of claim 1 wherein $-AR^1$ is selected from a moiety represented by the formula:

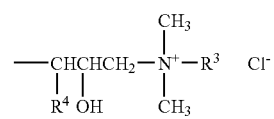

wherein $R^3$ is selected from $C_1$ to $C_{24}$ alkyl, benzyl and phenyl, and $R^4$ is chlorine or hydrogen.

6. A method of claim 5 wherein said -AR$^1$ moiety is 2-hydroxy-3-(trimethylammonium)propyl chloride.

7. A method of claim 1 wherein said active ingredient is selected from a skin conditioning and a hair conditioning agent.

8. A method of claim 7 wherein said hair conditioning agent is selected from silicone and silicone oil.

9. A method of claim 1 wherein said personal care composition comprises a surfactant, a water soluble agent and an active ingredient selected from a therapeutic agent, a conditioner, and a moisturizer.

10. A method of claim 9 wherein said water soluble agent is a silicone.

11. A method of claim 9 wherein said therapeutic agent is selected from detangling and wet combing agents, humectant, anti-acne agent, hair loss preventing agent, hair growth inhibiting agent, and herbal extract.

12. A method of claim 1 wherein said personal care composition comprises a water insoluble particulate or a water insoluble styling polymer.

13. A method of claim 12 wherein said insoluble particulate is selected from an antidandruff agent, a sunscreen, and an antimicrobial agent.

14. A method of claim 1 wherein said personal care composition is selected from a shampoo, liquid soap, soap bar, syndet bar, conditioning liquid bath oil, bubble bath, nail care product, hair removal product, deodorant, antiperspirant, skin care product, antiacne product, antiaging product, skin protectant, skin color product, hair colorant, pigmented skin colorant, body cleanser, shower gel, sunless tanning product, and a body wash.

15. A method of claim 14 wherein said personal care composition is a styling shampoo or a two-in-one conditioning shampoo.

16. A method of claim 5 wherein said chemically, cosmetically, or physiologically active agent is selected from particulate antidandruff agent(s), particulate antimicrobial agent(s), biocide(s), sunscreen agent(s), water-insoluble hair styling polymer(s) selected from (meth)acrylate copolymers and silicone grafted (meth)acrylates, fabric softener(s), fabric brightener(s), and fabric whitener(s).

17. A method of claim 14 wherein said pigmented skin colorant is selected from foundation cream, mascara, rouge, and lip products.

18. A method of claim 1 wherein said healthcare product is an oral care product.

19. A method of claim 18 wherein said oral care product is selected from mouth wash, toothpaste, tooth powder, tooth polish, tooth whitener, breath freshener, and denture adhesive.

20. A method of claim 1 wherein said *cassia* galactomannans in said cationically functionalized *cassia* galactomannan is obtained from *cassia tora* and *cassia obtusifolia*.

21. A method of claim 5 wherein said *cassia* galactomannans in said cationically functionalized *cassia* galactomannan is obtained from *cassia tora* and *cassia obtusifolia*.

22. A method of claim 6 wherein said *cassia* galactomannans in said cationically functionalized *cassia* galactomannan is obtained from *cassia tora* and *cassia obtusifolia*.

* * * * *